(12) United States Patent
Ichihashi et al.

(10) Patent No.: US 8,601,857 B2
(45) Date of Patent: Dec. 10, 2013

(54) CRYSTAL OSCILLATOR, AND MEASUREMENT METHOD USING SAME

(75) Inventors: Motoko Ichihashi, Kanagawa (JP); Atsushi Itoh, Kanagawa (JP)

(73) Assignee: Ulvac, Inc., Chigasaki-Shi (JP)

( * ) Notice: Subject to any disclaimer, the term of this patent is extended or adjusted under 35 U.S.C. 154(b) by 255 days.

(21) Appl. No.: 12/991,550

(22) PCT Filed: May 13, 2009

(86) PCT No.: PCT/JP2009/058930
§ 371 (c)(1),
(2), (4) Date: Nov. 8, 2010

(87) PCT Pub. No.: WO2009/139418
PCT Pub. Date: Nov. 19, 2009

(65) Prior Publication Data
US 2011/0061462 A1    Mar. 17, 2011

(30) Foreign Application Priority Data

May 14, 2008 (JP) .................................. 2008-127519

(51) Int. Cl.
*G01N 9/00* (2006.01)
*G01N 11/16* (2006.01)

(52) U.S. Cl.
USPC ........................................ 73/32 A; 73/54.26

(58) Field of Classification Search
USPC ................... 73/32 A, 54.25, 54.26, 54.41
See application file for complete search history.

(56) References Cited

U.S. PATENT DOCUMENTS

| | | | |
|---|---|---|---|
| 4,872,335 A | 10/1989 | Tsuruoka | |
| 5,741,961 A | 4/1998 | Martin | |
| 7,552,619 B2 * | 6/2009 | Andle | 73/32 A |
| 2004/0150428 A1 | 8/2004 | Itoh | |
| 2007/0144240 A1 | 6/2007 | Andle | |

FOREIGN PATENT DOCUMENTS

| | | |
|---|---|---|
| JP | 62-195538 | 8/1987 |
| JP | 10-115648 | 5/1998 |
| JP | 11-211705 | 8/1999 |
| JP | 4083621 B2 | 4/2008 |

OTHER PUBLICATIONS

C. Zhang, et al.; "Surface microstructures of TSM resonators and liquid properties measurement;" Sensors and Actuators; B 65; 2000; pp. 296-298 (3 Sheets.).

(Continued)

*Primary Examiner* — John Chapman, Jr.
(74) *Attorney, Agent, or Firm* — Kratz, Quintos & Hanson, LLP

(57) ABSTRACT

A crystal oscillator, and a measurement method using same are provided with which the density of a solution can be measured alone, or both the density and the viscosity of a solution can be measured at the same time using a single detector provided for the crystal oscillator. A material to be measured is contacted to the crystal oscillator, and the crystal oscillator that includes electrodes formed on both surfaces of a piezoelectric plate, and an uneven-surface formed either on one of the electrodes disposed on the side in contact with the material to be measured, or on a detector formed on the electrode is oscillated. An amount of change in frequency ($f_2$) that corresponds to the high-frequency side of two frequencies that represent a half value of a conductance maximum value of the crystal oscillator is measured to measure a density of the material.

7 Claims, 3 Drawing Sheets

(56) References Cited

OTHER PUBLICATIONS

International Search Report for International Application No. PCT/JP2009/058930 dated Jul. 22, 2009.

Chinese Office Action for counterpart Chinese Patent Application No. 200980117265.7 dated Dec. 26, 2012, with Japanese translation and partial English translation.

* cited by examiner

CRYSTAL OSCILLATOR, AND MEASUREMENT METHOD USING SAME

TECHNICAL FIELD

The present invention relates to a crystal oscillator, and a measurement method using same with which the density of a solution can be measured alone, or both the density and the viscosity of a solution can be measured at the same time.

BACKGROUND ART

The QCM (Quartz Crystal Microbalance) method that utilizes the resonance phenomenon of a crystal oscillator allows for the detection of even very small mass changes using a simple apparatus, not only for measurements in a gaseous phase but also in a liquid phase. For this reason, the QCM method has been widely used for, for example, gas sensors, film thickness sensors, chemical sensors, and biosensors that measure interactions of biological materials such as DNA and protein.

Conventionally, the QCM method is applied in a variety of measurements by being used to measure the resonant frequency that results from oscillation, or the resonant frequency obtained by sweeping a frequency using a device such as an impedance analyzer and a network analyzer.

In QCM measurement performed in a gaseous phase, only the mass of the material adhered to an electrode surface is detected as an amount of frequency change, and accordingly conversion into density is relatively easy.

However, in the measurement of solution density and viscosity, it has been difficult to separately measure the density and the viscosity of the solution using the conventional QCM method, because, unlike measurement in a gaseous phase, the frequency change due to the solution resistance on the oscillating surface of a crystal oscillator has a correlation with the product of density and viscosity.

Thus, if the density and viscosity were both unknown, the values of density and viscosity cannot be determined using the conventional QCM method.

As a countermeasure, U.S. Pat. No. 5,741,961 and U.S. Pat. No. 5,798,452 propose methods for measuring solution density and viscosity using a sensor provided with two or more detectors. At least one of the detectors is used as a reference detector that measures the frequency due to solution resistance, and the solution resistance component of the reference detectors is removed from the measurement results of the other detectors so as to measure the density and viscosity of the solution.

However, it is laborious to provide a plurality of detectors for a single piezoelectric plate, or to use a plurality of sensors. In addition to being laborious, it increases the manufacturing cost of the sensor. Another problem is the individual differences among the detectors.

Further, drawing a standard curve with a single sensor requires preparation of a plurality of standard samples, and it takes time to start the actual measurement. Further, because the density and viscosity can only be determined from the resonant frequency that contains the information of both density and viscosity, measurement accuracy is considerably low.

SUMMARY OF THE INVENTION

Problems that the Invention is to Solve

It is an object of the present invention to provide a crystal oscillator, and a measurement method using same with which the density of a solution can be measured alone, or both the density and the viscosity of a solution can be measured at the same time using a single detector provided for the crystal oscillator.

Means for Solving the Problems

In order to solve the foregoing problems, a measurement method of a first embodiment of the present invention includes: contacting a material to be measured to the crystal oscillator and oscillating the crystal oscillator that includes electrodes formed on both surfaces of a piezoelectric plate, and an uneven-surface formed either on one of the electrodes disposed on the side in contact with the material to be measured, or on a detector formed on the electrode; and measuring an amount of change in frequency ($f_2$) that corresponds to the high-frequency side of two frequencies that represent a half value of a conductance maximum value of the crystal oscillator, so as to measure a density of the material.

In a second embodiment according to the first embodiment, amounts of change of at least two of the frequencies on an admittance circle diagram of the crystal oscillator are measured to also measure a viscosity of the material.

In a third embodiment according to the second embodiment, the at least two frequencies on the admittance circle diagram are any two of frequencies ($f_1$, $f_2$) that represent the half value of the conductance maximum value of the crystal oscillator, and a resonant frequency ($f_s$) of the crystal oscillator.

In a fourth embodiment according to the first embodiment, the frequency ($f_2$) is obtained by directly measuring a frequency that corresponds to a susceptance minimum value ($B_{min}$) on an admittance circle diagram of the crystal oscillator.

In a fifth embodiment according to the first embodiment, the viscosity of the material is also measured by measuring amounts of change of at least two of the frequencies between two frequencies ($f_1$, $f_2$) that represent a half value of a conductance maximum value of the crystal oscillator.

In a sixth embodiment according to the fifth embodiment, the at least two frequencies are any two of the frequencies ($f_1$, $f_2$) that represent the half value of the conductance maximum value of the crystal oscillator, and a resonant frequency ($f_s$) of the crystal oscillator.

In a seventh embodiment according to the first embodiment, the frequency ($f_2$) is obtained through indirect measurement from (I) a frequency ($f_1$) that corresponds to the low-frequency side of two frequencies that represent a half value of a conductance maximum value of the crystal oscillator, and (II) a resonant frequency ($f_s$).

In an eighth embodiment according to the first embodiment, the measurement is made using a fundamental frequency or a higher-order wave of the crystal oscillator.

A crystal oscillator of a ninth embodiment of the present invention includes electrodes on both surfaces of a piezoelectric plate, and a density-measuring uneven-surface formed either on one of the electrodes disposed on the side in contact with a material to be measured, or on a detector formed on the electrode.

In a tenth embodiment according to the ninth embodiment, the uneven-surface is a surface with an arithmetic average roughness (Ra) of from 0.1 μm to 20 μm.

In an eleventh embodiment according to the ninth embodiment, the uneven-surface includes a plurality of grooves formed adjacent to one another.

Advantage of the Invention

The present invention overcomes the limitations of the conventional QCM method, and enables the measurement of solution density alone, or the simultaneous measurement of density and viscosity with ease using only a crystal oscillator that includes a single detector.

MODE FOR CARRYING OUT THE INVENTION

The crystal oscillator used in the present invention includes electrodes on the both surfaces of a piezoelectric plate, and an uneven-surface formed on the electrode disposed on the side in contact with a material to be measured, or on a detector formed on the electrode by vapor deposition or sputtering.

The uneven-surface can be formed on the electrode surface or the detector surface, for example, by making the surface of the crystal plate uneven such as patterned indented or roughed beforehand in a portion to be provided with the detector, or by depositing an electrode-forming metallic film on a surface of the crystal plate after subjected to limited polishing. The uneven-surface may be provided only in portions of the electrode surface or the detector.

Preferably, the uneven-surface is a surface with an arithmetic average roughness (Ra) of from 0.1 μm to 20 μm. With an Ra less than 0.1 μm, the density of the measured material cannot be measured, and accordingly viscosity cannot be determined. Above 20 μm, the crystal oscillator cannot maintain the state suited for measurement, possibly making the measured frequencies unstable, or failing to obtain frequencies.

Preferably, the uneven-surface has a groove, preferably a plurality of grooves. In this way, the uneven-surface can provide recesses for accepting the material to be measured. Preferably, the groove has a width of about 0.1 to 100 μm, and a depth of about 0.1 to 40 μm. Because the crystal plate oscillates in a certain direction parallel to the plate surface, the grooves are provided to extend in a direction crossing the oscillation direction of the crystal plate, preferably a direction perpendicular to the oscillation direction, in order to ensure trapping of the material to be measured in the grooves.

An embodiment of a measurement method of the present invention is described below, using the crystal oscillator described above.

First, the crystal oscillator is oscillated at a predetermined frequency, and a material to be measured is contacted to the electrode or the detector formed on the electrode.

Figure 1:
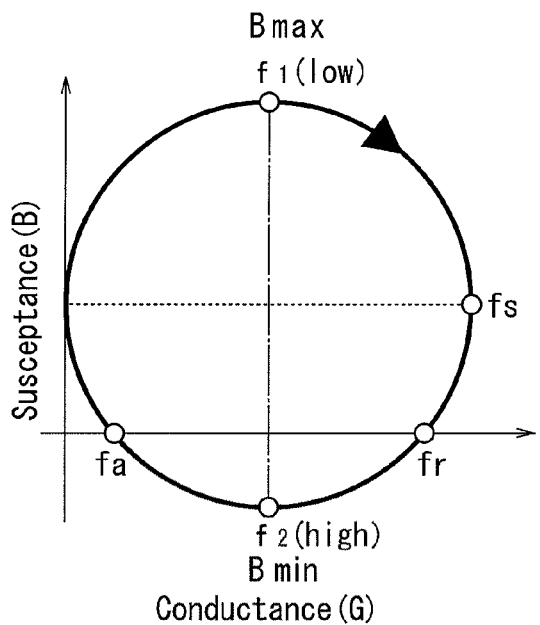
FIG. 1 is an explanatory view showing an admittance circle diagram of a crystal oscillator.

Measurement is made with regard to an amount of change in frequency ($f_2$) that corresponds to the high-frequency side of the two frequencies that represent the half value of the conductance maximum value of the crystal oscillator. Amounts of change of at least two frequencies on an admittance circle diagram (FIG. 1) that represents the characteristic of the crystal oscillator are also measured.

The amounts of frequency change on the admittance circle diagram are the same for the mass loading of the material, but the amounts of frequency change due to solution resistance become different for different frequencies.

Thus, for example, the amount of frequency change due to solution resistance for frequency $f_1$ that corresponds to the low-frequency side of the frequencies that represent the half value of the conductance maximum value of the crystal oscillator becomes twice as large as the amount of frequency change due to solution resistance for resonant frequency $f_s$. The amount of frequency change due to solution resistance is almost zero for the frequency $f_2$ that corresponds to the high-frequency side of the frequencies that represent the half value of the conductance maximum value of the crystal oscillator.

This can be understood from the following approximation formulae for the frequencies $f_1$, $f_s$, and $f_2$ in a solution.

$$\Delta f_1 = -\frac{2N f_0^2}{\sqrt{\rho_Q \mu_Q}} \frac{\Delta m}{A} - \frac{2N^{1/2} f_0^{3/2} \sqrt{\rho_L \eta_L}}{\sqrt{\pi \rho_Q \mu_Q}} \quad [\text{Formula 1}] \quad (1)$$

$$\Delta f_s = -\frac{2N f_0^2}{\sqrt{\rho_Q \mu_Q}} \frac{\Delta m}{A} - \frac{N^{1/2} f_0^{3/2} \sqrt{\rho_L \eta_L}}{\sqrt{\pi \rho_Q \mu_Q}} \quad [\text{Formula 2}] \quad (2)$$

$$\Delta f_2 = -\frac{2N f_0^2}{\sqrt{\rho_Q \mu_Q}} \frac{\Delta m}{A} \quad [\text{Formula 3}] \quad (3)$$

In the formulae (1) to (3), $f_0$ is the fundamental frequency, N the order of the higher-order wave (N=1, 3, 5, . . . ), $\eta_L$ the viscosity, $\rho_Q$ the density of the crystal oscillator, $\mu_Q$ the modulus of transverse elasticity of the crystal oscillator, $\Delta m$ the amount of mass change, A the electrode area, and $\rho_L$ the density of the solution.

By taking advantage of the natures of these frequencies, for example, the amount of frequency change in $f_2$, which does not depend on solution resistance, gives the mass of the material to be measured captured on the concave part of uneven-surface by the oscillating electrode of the crystal oscillator, upon measuring $f_1$, $f_2$, and $f_s$.

The mass so obtained from equation (3) can then be used to determine density, by dividing the mass by the previously measured or derived volume of the liquid captured on the concave part of uneven-surface.

Because the amounts of frequency change due to mass loading are the same on the admittance circle diagram of the crystal oscillator, the amount of change in $f_s$ is due to both solution resistance and mass loading. Similarly, the amount of change in $f_1$ is also due to both solution resistance and mass loading.

Thus, viscosity $\eta_L$ can be determined by substituting the density obtained from the amount of frequency change in $f_2$, and the amount of frequency change due to only the resistance component of the measured material into the following equation (4).

$$\Delta f_L = \Delta \frac{(f_1 - f_2)}{2} = -\frac{\sqrt{N} f_0^{3/2} \sqrt{\rho_L \eta_L}}{\sqrt{\pi \rho_Q \mu_Q}} \quad \text{[Equation 4]} \quad (4)$$

where $\Delta f_L$, is the amount of frequency change due to only the resistance component of the measured material on the oscillating surface of the crystal oscillator.

The frequency ($f_2$) can be obtained either directly by measuring the frequency that corresponds to the minimum value ($B_{min}$) of the susceptance in the admittance circle diagram, or indirectly from (I) the frequency ($f_1$) that corresponds to the low-frequency side of the two frequencies that represent the half value of the conductance maximum value of the crystal oscillator, and (II) the resonant frequency ($f_s$), using the relationship ($f_1+f_2$)/2=$f_s$.

The frequencies measured to obtain the amount of frequency change due to only the resistance component of the material to be measured on the oscillating surface of the crystal oscillator are not particularly limited, as long as they are at least two frequencies on the admittance circle diagram. The frequencies are not limited to $f_1$ and $f_2$, and may be $f_1$ and $f_s$, or $f_s$ and $f_2$.

The frequencies used for the measurement are not limited to fundamental waves, and higher-order waves of these frequencies also can be used. In this way, the pressure wave that occurs between the crystal oscillator and the liquid surface can be reduced, and a solution measurement is enabled in even smaller quantities, as described in JP-A-2005-98866.

The frequency measurements may be performed using a frequency counter by measuring the oscillation of the crystal oscillator, or by sweeping the frequencies using an impedance analyzer or a network analyzer.

The sensor portion including the sensor may be of, for example, a cup type, a liquid droplet placement type, or a flow-cell type. Measurement of solution density and viscosity is possible regardless of the shape of the sensor portion.

EXAMPLES

An example of the present invention is described below with reference to the accompanying drawings.

Figure 2:
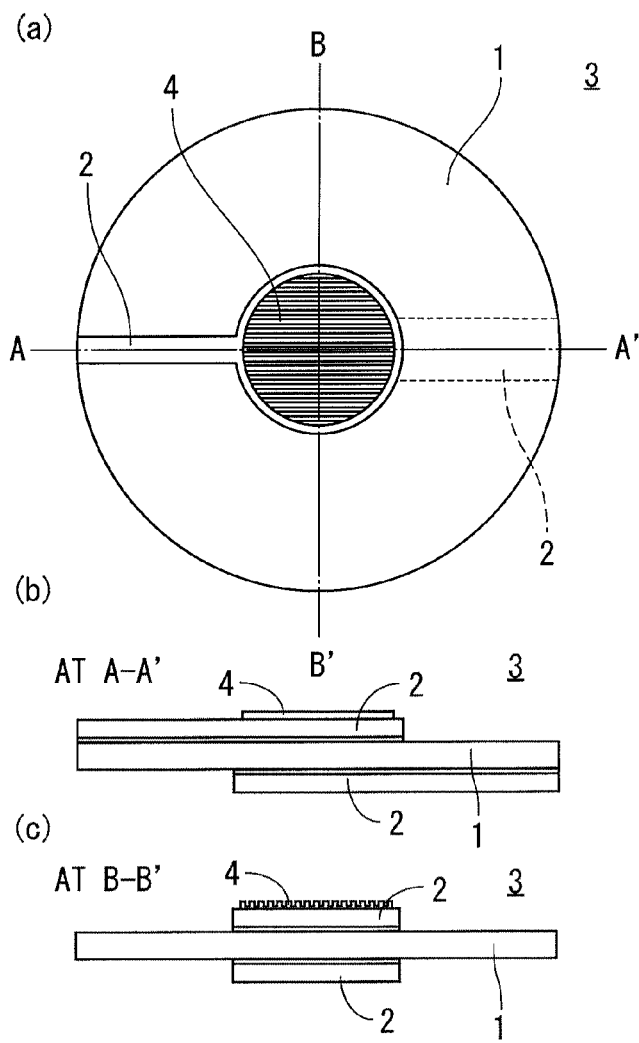
FIG. 2 shows (a) a plan view, (b) an A-A' cross sectional view, and (c) a B-B' cross sectional view of a crystal oscillator used in an example of the present invention.
Figure 3:
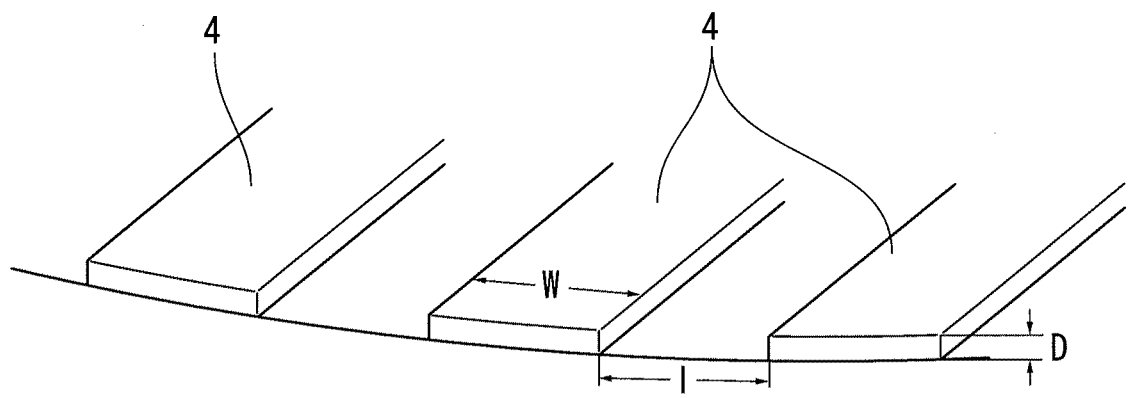
FIG. 3 is a perspective view explaining grooves provided for a detector of the crystal oscillator.

As illustrated in FIG. 2, a 27-MHz crystal oscillator 3 including gold electrodes 2, 2 on the both sides of a piezoelectric plate 1 was prepared. In the crystal oscillator 3, as illustrated in FIG. 3, a plurality of grooves 4 having a rectangular cross section is provided adjacent to one another on the surface of the gold electrode 2 in contact with a solution, so as to form a detector on the electrode 2.

The electrodes 2.2 were formed using gold that had a diameter of 2.7 mm. The width W and the interval I of the grooves 4 were both 5 μm. The depth D of the grooves was 600 nm.

Figure 4:
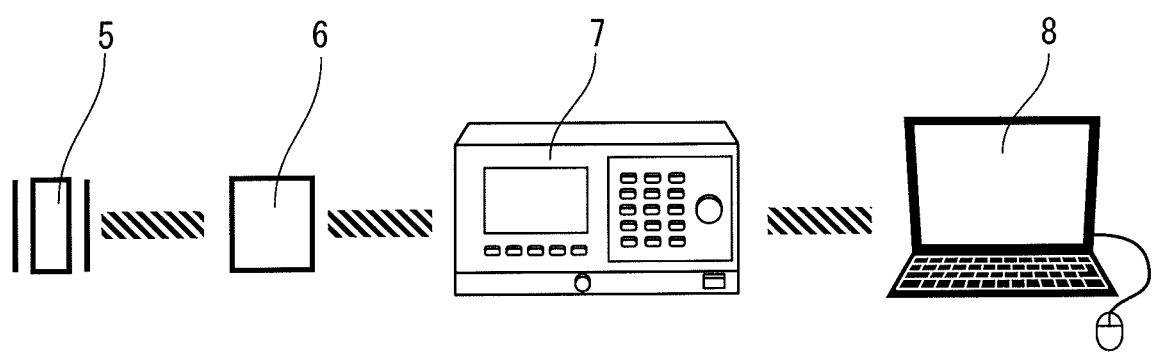
FIG. 4 is an explanatory diagram illustrating an apparatus configuration used in the measurement method of the example of the present invention.

The crystal oscillator 3 was placed in an aluminum block provided with an automatic stirring function and a temperature regulator. The crystal oscillator 3 as a sensor 5 was then connected, as illustrated in FIG. 4, to a frequency-measuring network analyzer 7 via an circuit 6, and the network analyzer 7 was adapted to send signals to a personal computer 8.

The sensor 5 was used to maintain the material to be measured to a liquid temperature of 25° C. during the measurement, which was performed as follows.

Frequencies were measured for a standard sample (deionized water; 500 μl), and for glycerol aqueous solutions of known density and known viscosity (10 wt %, 30 wt %, and 50 wt % samples; 500 μl each) placed on the electrode 2 of the crystal oscillator 3.

Table 1 below presents amounts of change in frequency $f_2$, resonant frequency $f_s$, and the frequency ($f_1-f_2$)/2 determined from $f_1$ and $f_2$. The resonant frequency $f_s$ was measured for comparison with the resonant frequency obtained by the conventional QCM method.

TABLE 1

| Glycerol (wt %) | $\Delta f_2$ | $\Delta f_s$ | $\Delta(f_1 - f_2)/2$ |
|---|---|---|---|
| 0 (standard solution) | −7070 | −15855 | −8795 |
| 10 | −7347 | −17418 | −10079 |
| 30 | −7620 | −21412 | −13792 |
| 50 | −7953 | −28697 | −20780 |

The amount of frequency change in $f_2$ was $\Delta f_2$=−7070 Hz for the standard sample using deionized water. From this, the amount of solution captured by the recesses formed in the detector on the electrode was found to be 213 pl.

Note that the calculation was made at the sensitivity 30 pg/Hz of the 27-MHz crystal oscillator 3, and at the density 0.997 g/cm³ of the deionized water at 25° C.

The detected value of resonant frequency $f_s$ in the conventional QCM method is the sum of the frequency detected as the mass of the sample captured by the concave of the detector, plus the frequency due to solution resistance. Thus, the measured amount of frequency change cannot be used to determine the amount of the solution of the detected mass captured by the concave.

The amount of the solution of the detected mass captured by the concave on the electrode 2 was 213 pl. Using this value, the densities of the 10 wt %, 30 wt %, and 50 wt % glycerol aqueous solutions were calculated from the amounts of frequency change of these samples.

Figure 5:
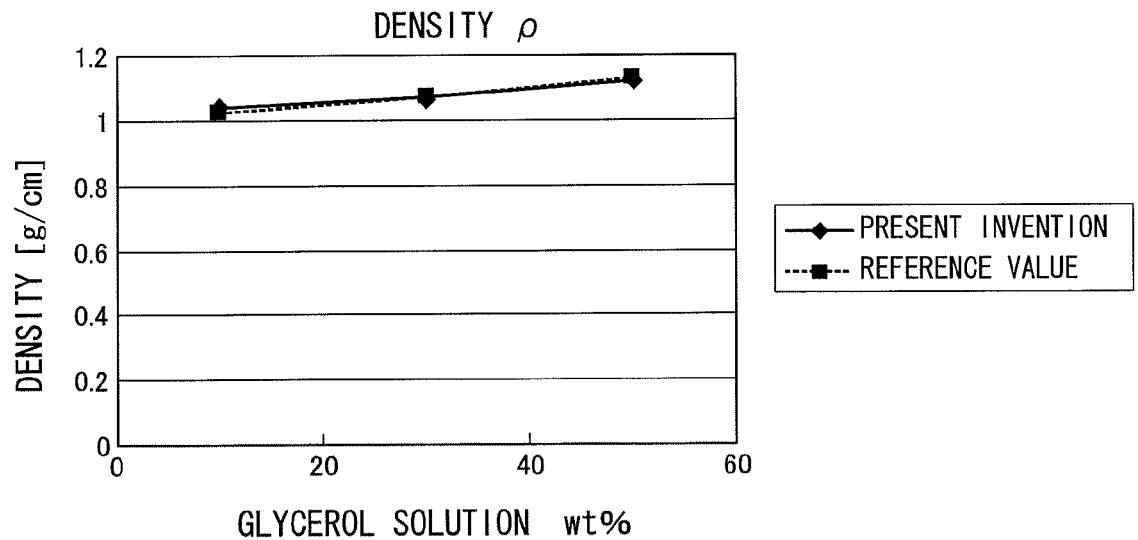
FIG. 5 is a graph comparing the density measurement result of the example and the densities presented in Kagaku Binran.

The results are presented in Table 2 below, and in the graph of FIG. 5.

TABLE 2

| Glycerol (wt %) | Density determined from frequency change ρ (g/cm³) | Density presented in Kagaku Binran ρ (g/cm³) |
|---|---|---|
| 10 | 1.0348 | 1.0207 |
| 30 | 1.0732 | 1.0706 |
| 50 | 1.1201 | 1.1239 |

The density values determined from the amounts of frequency change were close to the densities presented in Kagaku Binran (3rd ed., published in 1984).

Viscosities were determined from the amounts of frequency change in ($f_1-f_2$)/2 representing the frequency of only the solution resistance component on the oscillating surface of the crystal oscillator 3, using the densities obtained from the amounts of frequency change as above.

Note that the calculations were made at the density 2.65 g/cm³ of the crystal oscillator 3, and at the modulus of transverse elasticity 2.95×10¹¹ g/cm·S² of the crystal oscillator 3.

Figure 6:
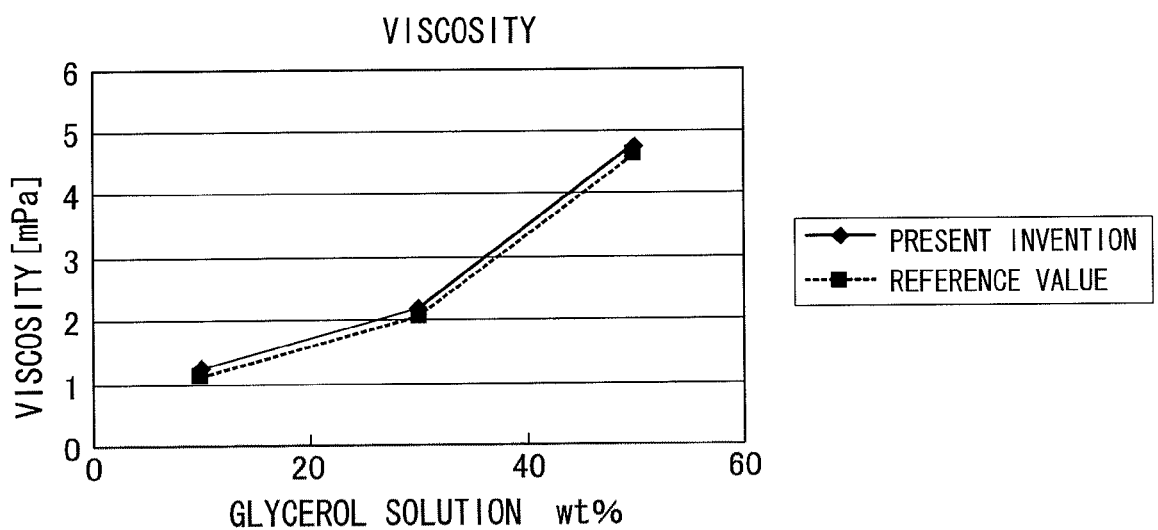
FIG. 6 is a graph comparing the viscosity measurement result of the example and the viscosities presented in Kagaku Binran.

Viscosities η were calculated by substituting the numerical values in equation (4). The results are presented in Table 3 below, and in the graph of FIG. 6.

TABLE 3

| Glycerol (wt %) | Viscosity determined from frequency change η (mPas) | Viscosity presented in Kagaku Binran η (mPas) |
| --- | --- | --- |
| 10 | 1.2228 | 1.1169 |
| 30 | 2.2076 | 2.0720 |
| 50 | 4.8015 | 4.6062 |

The viscosity values determined from the amounts of frequency change were close to the viscosities calculated using the values of Kagaku Binran as reference.

Note that the viscosities calculated using the values of Kagaku Binran as reference are values approximated from the values presented for temperatures around 25° C., because this handbook did not have values at 25° C.

These results show that solution density and viscosity can be accurately measured at the same time only with the single crystal oscillator 3 having one detector.

The foregoing example measured density and viscosity at the same time. However, only the density can be measured alone. When only the viscosity is needed, measurement of the viscosity alone is also possible of course based on the measured density.

INDUSTRIAL APPLICABILITY

The present invention can be used for the measurement of density and/or viscosity using a minute amount of solution.

DESCRIPTION OF REFERENCE NUMERALS AND SIGNS

1 Piezoelectric plate
2 Gold electrodes
3 Crystal oscillator
4 Grooves
5 Sensor
6 π Circuit
7 Network analyzer

The invention claimed is:

1. A measurement method that uses a crystal oscillator, wherein the method comprises:

contacting a material to be measured to the crystal oscillator and oscillating the crystal oscillator that includes electrodes formed on both surfaces of a piezoelectric plate, and an uneven-surface formed either on one of the electrodes disposed on the side in contact with the material to be measured, or on a detector formed on the electrode; and measuring an amount of change in frequency ($f_2$) that corresponds to the high-frequency side of two frequencies that represent a half value of a conductance maximum value of the crystal oscillator, so as to measure a density of the material, wherein amounts of change of at least two of the frequencies on an admittance circle diagram of the crystal oscillator are measured to also measure a viscosity of the material, and wherein said at least two frequencies on the admittance circle diagram are any two of frequencies (f1, f2) that represent the half value of the conductance maximum value of the crystal oscillator, and a resonant frequency (fs) of the crystal oscillator.

2. The method according to claim 1, wherein the frequency ($f_2$) is obtained by directly measuring a frequency that corresponds to a susceptance minimum value ($B_{min}$) on an admittance circle diagram of the crystal oscillator.

3. The method according to claim 1, wherein the frequency ($f_2$) is obtained through indirect measurement from (I) a frequency ($f_1$) that corresponds to the low-frequency side of two frequencies that represent a half value of a conductance maximum value of the crystal oscillator, and (II) a resonant frequency ($f_s$).

4. The method according to claim 1, wherein the measurement is made using a fundamental frequency or a higher-order wave of the crystal oscillator.

5. A measuring device comprising:

a crystal oscillator comprising electrodes on both surfaces of a piezoelectric plate, and a density-measuring uneven-surface formed either on one of the electrodes disposed on the side in contact with a material to be measured, or on a detector formed on the electrode, and a network analyzer, which is connected to the crystal oscillator, measuring an amount of change in frequency ($f_2$) that corresponds to the high-frequency side of two frequencies that represent a half value of a conductance maximum value of the crystal oscillator, so as to measure a density of the material, and measuring amounts of change of at least two of the frequencies on an admittance circle diagram of the crystal oscillator to also measure a viscosity of the material.

6. The crystal oscillator according to claim 5, wherein the uneven-surface is a surface with an arithmetic average roughness (Ra) of from 0.1 μm to 20 μm.

7. The crystal oscillator according to claim 5, wherein the uneven-surface includes a plurality of grooves formed adjacent to one another.

\* \* \* \* \*